US008411818B2

United States Patent
Sperschneider et al.

(10) Patent No.: US 8,411,818 B2
(45) Date of Patent: Apr. 2, 2013

(54) X-RAY TESTING METHOD AND X-RAY TESTING DEVICE

(75) Inventors: Eckhard Leonhard Sperschneider, Neubiberg (DE); Jan Rimbach, Erfurt (DE); Martin Sokolowski, Isen (DE); Timothy John McGann, Scarsdale, NY (US)

(73) Assignee: Matrix Technologies GmbH, Dachau (DE)

( * ) Notice: Subject to any disclaimer, the term of this patent is extended or adjusted under 35 U.S.C. 154(b) by 687 days.

(21) Appl. No.: 12/093,844

(22) PCT Filed: Nov. 13, 2006

(86) PCT No.: PCT/EP2006/010874
§ 371 (c)(1),
(2), (4) Date: Aug. 4, 2010

(87) PCT Pub. No.: WO2007/057144
PCT Pub. Date: May 24, 2007

(65) Prior Publication Data
US 2010/0290582 A1    Nov. 18, 2010

(30) Foreign Application Priority Data
Nov. 16, 2005 (DE) .......................... 10 2005 054 979

(51) Int. Cl.
*G01N 23/02* (2006.01)
(52) U.S. Cl. .................................................... 378/58

(58) Field of Classification Search .................... 378/58, 378/98.12, 62; 382/130, 132
See application file for complete search history.

(56) References Cited

U.S. PATENT DOCUMENTS

| 5,836,504 A | 11/1998 | Koike et al. |
| 2001/0040217 A1 | 11/2001 | Mizuoka et al. |

FOREIGN PATENT DOCUMENTS

| JP | 3-72249 A | 3/1991 |
| JP | 2001-50730 A | 2/2001 |

OTHER PUBLICATIONS

K. Feldmann et al., "Closed Loop Quality Control in Printed Circuit Assembly", IEEE Transactions on Components, Packaging, and Manufacturing Technology—Part A, vol. 17, No. 2 (1994) pp. 270-276.

*Primary Examiner* — Jurie Yun
(74) *Attorney, Agent, or Firm* — Millen, White, Zelano & Branigan, P.C.

(57) ABSTRACT

A first x-ray image of the circuit board that is equipped with components only on a first side with a first x-ray device (2) that produces transmission images and a second x-ray image of a circuit board that is equipped with components on both sides with a second x-ray device (4) that produces transmission images are recorded in an x-ray testing method for checking circuit boards that are equipped with components on two sides, in particular for checking soldered joints. A test x-ray image is then evaluated in a computer unit in which the second side that is equipped with components is displayed in enhanced form by forming a function from the pixel values of the first x-ray image and the corresponding pixel values of the second x-ray image.

13 Claims, 1 Drawing Sheet

X-RAY TESTING METHOD AND X-RAY TESTING DEVICE

Figure 1:
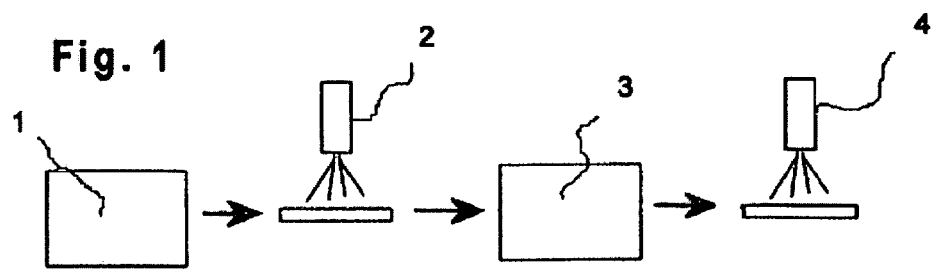

This invention relates to an x-ray testing method and an x-ray testing device for examining objects. In particular, the invention relates to an x-ray testing method and an x-ray testing device for x-raying from two sides, i.e., circuit boards equipped with electronic components on the top and the bottom.

In the manufacturing of circuit boards in surface-mounted technology (SMT), the so-called two-sided reflow process, in which both the top as well as the bottom of the circuit board are assembled, is being increasingly applied. In this case, a circuit board passes through a production line twice or through two production lines that are located behind one another, whereby for the top as well as for the bottom, the production steps of soldering paste pressing, assembly and reflow soldering (reflow) are carried out separately in succession.

It is known to check the quality of the soldered joints of the circuit board by a transmission process, in which the circuit board is x-rayed vertically and an image is made. This makes it possible to check the soldered joints when only one side of the circuit board is assembled. In the case of a circuit board that is assembled on both sides, components and soldered joints can be superimposed and thus make it difficult to evaluate the soldered joints.

It is also known to use x-ray systems for examining circuit boards that are assembled on both sides that make possible a reconstruction of a cross-sectional plane of the soldered joints of the top as well as a cross-sectional plane of the soldered joints of the bottom from x-ray images. It is known to evaluate these cross-sectional planes from images at various angles by computer tomography processes.

It is disadvantageous in this process that the quality of the reconstructed cross-sectional plane depends essentially on the available number of projections. In this case, projections must be made under different angles that deviate as much as possible from one another. This results in a long measuring period by the mechanical process into the next angular position and by the exponentially-increasing volume of data. In projections using x-rays, one factor is that each projection must be integrated over a certain period to reduce noise in the image as much as possible.

Laminography processes and tomosynthesis processes are also known. In the laminography processes, the image recording is carried out in slices by the image recording being focused on a specific slice. In the tomosynthesis process, multiple x-ray images are recorded under various angles and from these, a picture of a slice or a section is evaluated in a computer.

It is disadvantageous in this known process that they are relatively expensive.

It is therefore the object of this invention to make available an x-ray testing method and an x-ray testing device with which it is possible to display two or more planes of an object in a simple way.

This object is achieved by an x-ray testing method with the features of claim 1 and an x-ray testing device with the features of claim 12 as well as an assembly unit with the features of claim 13. Additional advantageous developments are indicated in the subclaims.

In the x-ray testing method according to the invention for checking circuit boards that are equipped on two sides with components, in particular for checking the soldered joints, a first x-ray image of the circuit board that is equipped with components only on a first side with a first x-ray device that produces transmission images is recorded in a first step, and then a second x-ray image of a circuit board that is equipped with components on both sides with a second x-ray device that produces transmission images is recorded.

A test x-ray image is then evaluated in a computer unit in which the second side that is equipped with components is displayed in enhanced form by a function being formed from the pixel values of the first x-ray image and the corresponding pixel values of the second x-ray image.

Thus, it is possible to display the second side that is equipped with components by the test x-ray image without shadows by the first side preventing checking. In addition, it is advantageous that an x-ray device that is relatively readily available for transmission images is sufficient for the process according to the invention.

Advantageously, the function for the test x-ray image comprises a subtraction of the pixel values of the first x-ray image from the pixel values of the second x-ray image.

As a result, in the ideal case, the image of the assembly is filtered out, and the soldered joints filter[s] out the first side of the circuit board, and the test x-ray image depicts in good quality the assembly of the second side and the soldered joints thereof.

In an advantageous embodiment of the process, the function for the test x-ray image comprises a quotient formation from the pixel values of the first x-ray image and the pixel values of the second x-ray image and/or a function of the first and second derivative of the pixel values of image object edges of the first and/or second x-ray image.

Since the absorption process of the x-ray radiation is not altered linearly with increasing material strength, the absorption curve or gamma curve is not a straight line.

Different materials, such as components, circuit boards, copper layers, etc., have a varying absorption behavior. Also, a detector for x-ray radiation in the x-ray device distorts the gray-scale values based on the image content, for example in areas of high contrast, such as on edges, or in the case of crosstalk on the CCD sensor. To avoid this, other mathematical functions of the image values of associated pixels of the two x-ray images can be used. Also, functions can take into consideration the pixel environment, such as, for example, the derivative of the gray-scale values in the area of the edges. In general, the depicted problematic effects can be avoided by a preprocessing of the recorded x-ray images. To this end, for example, a recording of an absorption curve by calibration with test circuit boards can also be used or in general a calibration by means of additional edge parameters.

Advantageously, an orientation and image scale adjustment by pattern recognition and/or edge alignment is carried out for recording a second x-ray image that is identical to (covering the same area as) the first x-ray image. The orientation can be carried out by searching for patterns and/or edges according to CAD-value specifications in the first and/or second x-ray image.

An important requirement of the evaluation of a test x-ray image is that both x-ray images be identical. This can be achieved by an approximately identical recording 5 position to circumvent, e.g., the influence of the parallax. The orientation of the second image just like the determination of the image size can then be carried out based on the second x-ray image and the detection of patterns or the orientation on the edges. Advantageously, in the recording of the first x-ray image, the orientation for the x-ray images of the second side is already optimized, e.g., by design or CAD data being used for the orientation.

In a more advantageous embodiment, an individual x-ray image of a master circuit board that is assembled on only one side is used, and a test x-ray image of the second size of a number of circuit boards is determined with this first x-ray image. In addition, test x-ray images can be determined with the help of the first x-ray images of master circuit boards in each case, both for the top and the bottom of the circuit board.

This makes it possible to check the soldered joints of the top as well as the bottom with only a recording of the circuit boards, already assembled on both sides, in each case on the end of the assembly in an x-ray device, by in each case a test x-ray image being determined for the top and the bottom. It is then only necessary to produce a master circuit board, which is assembled only on the top, and also one that is assembled only on the bottom. From these two master circuit boards, x-ray images are made and with the latter, in each case a test x-ray image of the top and the bottom can be determined from the images of the circuit boards that are assembled on both sides during production.

In the assembly of circuit boards, a first x-ray image can be recorded and stored for each circuit board, and then a second x-ray image can be recorded for each circuit board. The circuit boards can be passed through the assembly device and an x-ray device twice, and the x-ray device is used as a first and second x-ray device.

Thus, the process according to the invention can be used in existing assembly units with slight modifications of the assembly unit.

After a first assembly of one side in a first assembly device, the first x-ray image can be made in the first x-ray device, and after a second assembly of the second side in a second assembly device, the second x-ray image can be made in the second x-ray device.

As a result, a quick passing-through of the circuit boards is possible by the assembly with components. In particular, an x-ray device makes possible a time-saving recording of x-ray images according to the transmission process.

The object is also achieved by an x-ray testing device with the features of claim 12 as well as an assembly unit with the features of claim 13, which have the same, already described advantages.

Figure 2A:
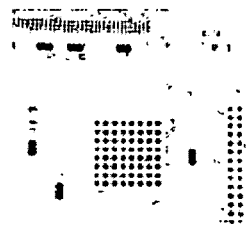
Figure 2B:
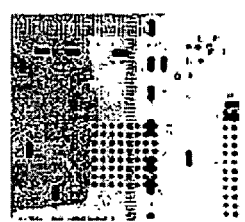
Figure 2C:
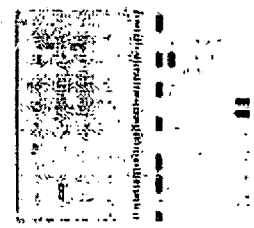
Figure 3A:
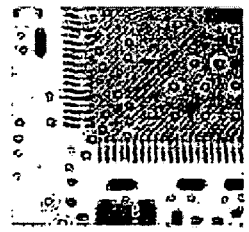
Figure 3B:
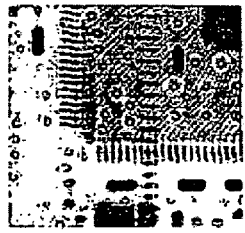
Figure 3C:

An embodiment of the process according to the invention regarding the x-ray and the x-ray system is explained in more detail in the drawings below. In the latter:

FIG. 1 shows diagrammatically the sequence of the process according to the invention in the x-raying of circuit boards, FIG. 2a shows a cutaway of an x-ray image of a circuit board that is assembled only on the top, FIG. 2b shows the cutaway of FIG. 2a of the circuit board that is assembled on the top and bottom, FIG. 2c shows the picture of the bottom of the cutaway of FIG. 2a, which was obtained with the process according to the invention, FIG. 3a shows a cutaway of an x-ray image of a circuit board that is assembled only on the top, FIG. 3b shows the cutaway of FIG. 3a of the circuit board that is assembled on the top and bottom, FIG. 3c shows the picture of the bottom of the cutaway of FIG. 3a, which was obtained with the process according to the invention.

FIG. 1 shows diagrammatically the sequence of the process according to the invention for the x-raying of circuit boards. After a first assembly of a first side of the circuit boards in a first assembly device 1, the circuit boards, indicated by the arrow, are transported into a first x-ray device 2, and a first x-ray image is recorded. The image that is made is stored in a computer unit that is not shown. Then, the circuit boards are assembled on the second side in a second assembly device 3 with components that are soldered on. In a second x-ray device 4, a second x-ray image is recorded. From the second x-ray image and the first x-ray image, the computer unit evaluates an x-ray test image, in this example by the first x-ray image being subtracted by pixels from the second x-ray image that is oriented on the same scale and the same perspective as the first x-ray image. In this case, the mutual orientation of the first and second x-ray images can be carried out in scale and perspective distortion even by an image processing in the computer unit.

In FIG. 2a, a cutaway of a first x-ray image of a circuit board that is assembled only on the top is shown. The soldered joints in this case come out clearly as dark shadows. FIG. 2b shows the same image cutaway of a second x-ray image, which is oriented exactly the same and has the same scale, of the circuit board that is now assembled on two sides. The circuit board that is assembled on the top and bottom now shows soldered joints approximately in the middle of the image, which lie above one another on the top and bottom, cover one another and prevent a conventional test.

FIG. 2c shows the corresponding cutaway of the evaluated test x-ray image of the bottom of the circuit board, which was obtained with the process according to the invention. In this case, the first x-ray image of FIG. 2a was subtracted from the second x-ray image of FIG. 2b. The previously partially covered soldered joints in the line of soldered joints that passes through vertically can now be evaluated, since the elements of the bottom of the circuit boards in the x-ray test image are greatly accentuated.

FIG. 3a shows a cutaway of a first x-ray image of a circuit board that is assembled only on the top, and FIG. 3b shows the cutaway of FIG. 3a of the circuit board that is assembled on the top and bottom, corresponding to the example of FIG. 2a and FIG. 2b.

The corresponding cutaway of FIG. 3c shows an x-ray test image, which in turn the examination of a soldered joint that is covered in FIG. 3b in the center of the image at the point of intersection of the two component connection series on the top and bottom. Contrary to the example of FIG. 2a to FIG. 2b, the x-ray test image was evaluated by a function that does not consist of a subtraction alone, but rather also contains a quotient formation. As a result, it is more readily possible to take into consideration the nonlinear absorption behavior to emphasize the image of the bottom more strongly.

Owing to the design with two x-ray devices according to the transmission process, which can make images very quickly, testing can be done without slowing the assembly speed.

REFERENCE SYMBOLS

1 First assembly device
2 First x-ray device
3 Second assembly device
4 Second x-ray device

The invention claimed is:

1. X-ray testing method for checking circuit boards that are equipped with components on two sides, for checking soldered joints, with the steps:
   taking a first x-ray image of a circuit board that is equipped with components only on a first side with a first x-ray device (2) that produces transmission images,
   taking a second x-ray image of at least one other circuit board that is equipped with components on both a first and a second side with a second x-ray device (4) that produces transmission images,
   evaluating a test x-ray image in a computer unit, in which the second side that is equipped with the components is displayed in enhanced form by forming a function from pixel values of the first x-ray image and corresponding pixel values of the second x-ray image, and wherein the function for the text x-ray image comprises a quotient formation from the pixel values of the first x-ray image and the pixel values of the second x-ray image.

2. X-ray testing method according to claim 1, wherein the function for the test x-ray image comprises a subtraction of the pixel values of the first x-ray image from the pixel values of the second x-ray image.

3. X-ray testing method according to claim 1, wherein the function for the test x-ray image is a function of the first and second derivatives of the pixel values of image object edges of the first and/or second x-ray image.

4. X-ray testing method according to claim 1, wherein for recording the second x-ray image covering the same area as the first x-ray image, an orientation and image scale adjustment is carried out by pattern recognition and/or edge alignment.

5. X-ray testing method according to claim 1, wherein patterns and/or edges according to CAD value requirements are sought for identical x-ray images for orientation and for image scale adjustment of the first and/or second x-ray image.

6. X-ray testing method according to claim 1, wherein the first x-ray image is an individual x-ray image of a master circuit board that is assembled on only one side, and wherein text x-ray images of the second sides of at least two other circuit boards is determined with this first x-ray image.

7. X-ray testing method according to claim 6, wherein the test x-ray images are determined using first x-ray images of master circuit boards for both the first and the second sides of the circuit board.

8. X-ray testing method according to claim 1, wherein in an assembly of circuit boards, the first x-ray image is recorded and stored for each circuit board, and then the second x-ray image is recorded for each circuit board.

9. X-ray testing method according to claim 8, wherein the circuit boards are passed through an assembly device and an x-ray device twice, and the x-ray device is used as the first and second x-ray device.

10. X-ray testing method according to claim 8, wherein after a first assembly of one side in a first assembly device (1), the first x-ray image is made in the first x-ray device (2), and after a second assembly of the second side in a second assembly device (3), the second x-ray image is made in the second x-ray device (4).

11. Assembly unit for circuit boards with two assembly devices and two x-ray devices, wherein a process according to claim 10 proceeds on said assembly unit.

12. X-ray testing device with at least one x-ray device, which produces transmission images, and a computer unit, wherein a process according to claim 1 proceeds on the latter.

13. X-ray testing method for checking circuit boards that are equipped with components on two sides, for checking soldered joints, with the steps:

taking a first x-ray image of a circuit board that is equipped with components only on a first side with a first x-ray device (2) that produces transmission images, taking a second x-ray image of at least one other circuit board that is equipped with components on both a first and a second side with a second x-ray device (4) that produces transmission images, evaluating a test x-ray image in a computer unit, in which the second side that is equipped with the components is displayed in enhanced form by forming a function from pixel values of the first x-ray image and corresponding pixel values of the second x-ray image, and wherein the first x-ray image is an individual x-ray image of a master circuit board that is assembled on only one side, and wherein test x-ray images of the second sides of at least two other circuit boards is determined with this first x-ray image.

* * * * *

UNITED STATES PATENT AND TRADEMARK OFFICE
CERTIFICATE OF CORRECTION

PATENT NO.         : 8,411,818 B2
APPLICATION NO.    : 12/093844
DATED              : April 2, 2013
INVENTOR(S)        : Eckhard Leonhard Sperschneider et al.

It is certified that error appears in the above-identified patent and that said Letters Patent is hereby corrected as shown below:

In the Claims:

Column 5, line 28, reads "text", should read --test--.

Signed and Sealed this
Twenty-third Day of July, 2013

Teresa Stanek Rea
*Acting Director of the United States Patent and Trademark Office*